US008786444B2

(12) United States Patent
Watson et al.

(10) Patent No.: US 8,786,444 B2
(45) Date of Patent: Jul. 22, 2014

(54) SYSTEMS AND METHODS FOR DETERMINING SIGNAL QUALITY OF A PHYSIOLOGICAL SIGNAL USING A WAVELET TRANSFORM AND AN IDENTIFIED NOISE FLOOR

(71) Applicant: Nellcor Puritan Bennett Ireland, Mervue (IE)

(72) Inventors: James Nicholas Watson, Dunfermline (GB); Paul Stanley Addison, Edinburgh (GB); Edward M. McKenna, Boulder, CO (US); James P. Ochs, Seattle, WA (US)

( * ) Notice: Subject to any disclaimer, the term of this patent is extended or adjusted under 35 U.S.C. 154(b) by 0 days.

(21) Appl. No.: 13/746,291

(22) Filed: Jan. 21, 2013

(65) Prior Publication Data

US 2013/0138357 A1 May 30, 2013

Related U.S. Application Data

(63) Continuation of application No. 12/497,824, filed on Jul. 6, 2009, now Pat. No. 8,358,213.

(60) Provisional application No. 61/080,982, filed on Jul. 15, 2008.

(51) Int. Cl.
*G08B 21/00* (2006.01)
(52) U.S. Cl.
USPC ............. 340/573.1; 340/539.12; 600/500; 702/19
(58) Field of Classification Search
USPC .......... 340/539.12, 573.1; 702/1, 19; 600/500
See application file for complete search history.

(56) References Cited

U.S. PATENT DOCUMENTS

| 4,289,141 | A | 9/1981 | Cormier |
| 5,439,483 | A | 8/1995 | Duong-Van |
| 5,590,650 | A | 1/1997 | Genova |
| 5,632,272 | A | 5/1997 | Diab et al. |
| 5,778,881 | A | 7/1998 | Sun et al. |
| 5,795,304 | A | 8/1998 | Sun et al. |
| 5,797,840 | A | 8/1998 | Akselrod |
| 5,827,195 | A | 10/1998 | Lander |
| 5,967,995 | A | 10/1999 | Shusterman et al. |

(Continued)

FOREIGN PATENT DOCUMENTS

| JP | 09-084776 | 3/1997 |
| WO | WO 01/25802 | 4/2001 |

(Continued)

OTHER PUBLICATIONS

Addison, Paul S., "The Illustrated Wavelet Transform Handbook," Taylor & Francis Group, 2002.

(Continued)

*Primary Examiner* — Jeffery Hofsass
(74) *Attorney, Agent, or Firm* — Shvarts & Leiz LLP

(57) ABSTRACT

A method and system are provided for evaluating in patient monitoring whether a signal is sensed optimally by receiving a signal, transforming the signal using a wavelet transform, generating a scalogram based at least in part on the transformed signal, identifying a pulse band in the scalogram, identifying a characteristic of the pulse band, determining, based on the characteristic of the pulse band, whether the signal is sensed optimally; and triggering an event. The characteristics of the pulse band and scalogram may be used to provide an indication of monitoring conditions.

20 Claims, 17 Drawing Sheets
(3 of 17 Drawing Sheet(s) Filed in Color)

(56) References Cited

U.S. PATENT DOCUMENTS

| | | |
|---|---|---|
| 6,002,952 A | 12/1999 | Diab et al. |
| 6,036,653 A | 3/2000 | Baba et al. |
| 6,094,592 A | 7/2000 | Yorkey |
| 6,095,984 A | 8/2000 | Amano et al. |
| 6,117,075 A | 9/2000 | Barnea |
| 6,129,675 A | 10/2000 | Jay |
| 6,135,966 A | 10/2000 | Ko |
| 6,171,257 B1 | 1/2001 | Weil et al. |
| 6,171,258 B1 | 1/2001 | Karakasoglu et al. |
| 6,208,951 B1 | 3/2001 | Kumar et al. |
| 6,293,915 B1 | 9/2001 | Amano et al. |
| 6,325,761 B1 | 12/2001 | Jay |
| 6,361,501 B1 | 3/2002 | Amano et al. |
| 6,393,311 B1 | 5/2002 | Edgar, Jr. et al. |
| 6,561,986 B2 | 5/2003 | Baura |
| 6,566,251 B2 | 5/2003 | Allen et al. |
| 6,608,934 B2 | 8/2003 | Scheirer |
| 6,654,623 B1 | 11/2003 | Kastle |
| 6,810,277 B2 | 10/2004 | Edgar, Jr. et al. |
| 6,931,269 B2 | 8/2005 | Terry |
| 7,001,337 B2 | 2/2006 | Dekker |
| 7,020,507 B2 | 3/2006 | Scharf |
| 7,035,679 B2 | 4/2006 | Addison |
| 7,043,293 B1 | 5/2006 | Baura |
| 7,054,453 B2 | 5/2006 | Causevic |
| 7,054,454 B2 | 5/2006 | Causevic et al. |
| 7,079,888 B2 | 7/2006 | Oung |
| 7,171,269 B1 | 1/2007 | Addison |
| 7,173,525 B2 | 2/2007 | Albert |
| 7,203,267 B2 | 4/2007 | De Man et al. |
| 7,225,013 B2 | 5/2007 | Geva et al. |
| 7,254,500 B2 | 8/2007 | Makeig |
| 7,289,835 B2 | 10/2007 | Mansfield |
| 7,515,949 B2 | 4/2009 | Norris |
| 7,519,488 B2 | 4/2009 | Fu |
| 7,523,011 B2 | 4/2009 | Akiyama et al. |
| 2003/0163057 A1 | 8/2003 | Flick et al. |
| 2005/0043616 A1 | 2/2005 | Chinchoy |
| 2006/0209631 A1 | 9/2006 | Melese et al. |
| 2006/0211930 A1 | 9/2006 | Scharf et al. |
| 2006/0229519 A1 | 10/2006 | Fujiwara et al. |
| 2006/0258921 A1 | 11/2006 | Addison et al. |
| 2006/0265022 A1 | 11/2006 | John et al. |
| 2007/0021673 A1 | 1/2007 | Arbel et al. |
| 2007/0073120 A1 | 3/2007 | Li et al. |
| 2007/0073124 A1 | 3/2007 | Li et al. |
| 2007/0167694 A1 | 7/2007 | Causevic et al. |
| 2007/0167851 A1 | 7/2007 | Vitali et al. |
| 2007/0282212 A1 | 12/2007 | Sierra et al. |
| 2008/0045832 A1 | 2/2008 | McGrath |
| 2008/0082018 A1 | 4/2008 | Sackner et al. |
| 2008/0214903 A1 | 9/2008 | Orbach |
| 2008/0243021 A1 | 10/2008 | Causevic et al. |
| 2009/0326386 A1 | 12/2009 | Sethi et al. |

FOREIGN PATENT DOCUMENTS

| | | |
|---|---|---|
| WO | WO 01/62152 | 8/2001 |
| WO | WO 03/055395 | 7/2003 |
| WO | WO 2004/105601 | 12/2004 |
| WO | WO 2005/096170 | 10/2005 |
| WO | WO 2006/085120 | 8/2006 |

OTHER PUBLICATIONS

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Leonard, Paul A., Clifton, David, Addison, Paul S., Watson, James N., Beattie, Tom, "An Automated Algorithm for Determining Respiratory Rate by Photoplethysmogram in Children," Acta Paediatricia, 2006; 95: 1124-1128.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Yamada, Michio, "Wavelet Analysis and Its Application," Journal of the Institute of Electronics, Information and Communication Engineers, vol. 76, No. 5, May 1993, pp. 518-528.

SYSTEMS AND METHODS FOR DETERMINING SIGNAL QUALITY OF A PHYSIOLOGICAL SIGNAL USING A WAVELET TRANSFORM AND AN IDENTIFIED NOISE FLOOR

CROSS-REFERENCE TO RELATED APPLICATION

This application is a continuation of U.S. patent application Ser. No. 12/497,824, filed Jul. 6, 2009, which claims the benefit of U.S. Provisional Application No. 61/080,982, filed Jul. 15, 2008, all of which are incorporated herein by reference in their entireties.

SUMMARY

The present disclosure relates to signal processing and, more particularly, the present disclosure relates to using continuous wavelet transforms for processing, for example, a photoplethysmograph (PPG) signal. PPG signals are used in a variety of fields, including in medical monitoring devices, such as a pulse oximeter. A pulse oximeter is a device that is capable of indirectly measuring blood oxygen saturation and is typically used by healthcare providers as a monitoring device for patients. The oximeter generally uses a light emitter than shines through a monitoring site or point on a patient. A photodetector or other sensor may be used to receive the light that has passed through the monitoring site. The light passing through the site may be measured and analyzed to determine the patient's blood oxygen saturation using, for example a scalogram generated by wavelet-transforming the PPG signal.

Since oxygen is critical to sustain human life, monitoring patients' blood oxygen saturation is one important indicator of a patient's physiological condition. If blood oxygen saturation levels determined by the oximeter are low, out of range, or below a certain threshold, this may be an indication that the patient's physiological condition is poor. This could also be an indication that the PPG signal is not being sensed optimally. For example, it could indicate that the location or some aspect of the oximeter monitoring site is not optimal, or that there is some problem with the oximeter components or monitoring technique, such as the quality, intensity, or frequency of the light, or other problem. Examples of monitoring location problems may include human error in sensor placement, patient's position impeding blood flow at the monitoring location, and others. With respect to light quality problems, oximeter readings may sometimes be improved if light intensity is changed.

In the various embodiments disclosed herein, features of a PPG scalogram are analyzed to determine whether the PPG signal is being sensed optimally, and to trigger a corrective action. For example, the scalogram may be analyzed to determine whether the sensor is optimally located. In response, an alert may be triggered prompting an attendant to reposition the sensor. As another example, the scalogram may be analyzed to determine whether the quality or intensity of the light used is not optimal. In response, a control signal may be generated to change the light.

One way to perform the analysis may include identifying features of the scalogram, for example, features of a pulse band, such as shape and type, marker regions, and characteristic features located near the pulse band. Another technique may be provided by comparing features of the scalogram against, for example, selectable thresholds, other scalograms having known and distinct aspects and features, or other comparative elements. These techniques are further described herein. Although the embodiments herein are discussed in reference to use with a pulse oximeter, they are equally applicable to other types of devices, including continuous non-invasive blood pressure (CNIBP) measurement devices. Systems and methods for calculating CNIBP are described in Chen et al. U.S. Pat. No. 6,566,251 and Sethi et al. U.S. patent application Ser. No. 61/076,955 and Ser. No. 12/242,238, filed Jun. 30, 2008 and Sep. 30, 2008, respectively, each of which are incorporated by reference herein in their entireties.

An embodiment may be provided by receiving a signal, such as a photoplethysmograph signal, transforming the signal using a wavelet transform, and generating a scalogram based at least in part on the transformed signal. The scalogram may be analyzed by identifying a pulse band in the scalogram and a characteristic of the pulse band. Based at least in part on the characteristic of the pulse band, a determination may be made as to whether the signal is sensed optimally. An event may also be triggered.

A characteristic of the pulse band may be identified by obtaining an incremental slice of the pulse band, and may comprise, for example, a height, width, amplitude, strength, or shape of the pulse band. In some embodiments, the characteristics may be compared to a threshold value. If the characteristic does not correspond to the threshold value, an event may trigger. Some examples of events include: sending a control signal to a light associated with the signal, an alert, and moving a sensor. Alerts may be, for example, an indication of use of increased light intensity, an indication of use of decreased light intensity, an indication to move the sensor, an indication to move the sensor closer to an artery, an indication to move the sensor away from an artery, an indication that the sensor is not optimally located, an indication to examine a patient, and an indication of use of a second sensor.

Another aspect of the embodiment includes generating at least a second scalogram based at least in part on the signal; and comparing at least two of: the scalogram, the second scalogram, and the threshold value. A feature of a marker region may also be identified, such as at least one characteristic feature positioned at one or more scales above or below the pulse band.

Another embodiment is directed to a system comprising: a signal generator for generating a signal, such as a photoplethysmograph signal, a processor coupled to the signal generator, and a display. The signal generator may be, for example, a pulse oximeter coupled to a sensor, a blood pressure monitor, or other device. The processor is capable of receiving the signal, transforming the signal using a wavelet transform, and generating a scalogram based at least in part on the transformed signal. The processor may also be used to identify a pulse band in the scalogram, and a characteristic of the pulse band. Based at least in part on the characteristic of the pulse band, the processor may determine whether the signal is sensed optimally. The display is for viewing the scalogram.

In an embodiment, the processor may identify the characteristic of the pulse band by obtaining an incremental slice of the pulse band. Some of the characteristics of the pulse band may include: a height, width, amplitude, strength, and shape. The processor is also capable of comparing the characteristic to a threshold value. In some embodiments, if the characteristic does not correspond to the threshold value, the processor may trigger an event. An event may be, for example, sending a control signal to a light associated with the signal, an alert, and moving a sensor. Some examples of alerts may include: an indication of use of increased light intensity, an indication of use of decreased light intensity, an indication to move the sensor, an indication to move the sensor closer to an artery, an indication to move the sensor away from an artery, an indication that the sensor is not optimally located, an indication to examine a patient, and an indication of use of a second sensor.

In another embodiment, the processor is capable of: generating at least a second scalogram based at least in part on the signal; and comparing at least two of: the scalogram, the second scalogram, and the threshold value. The processor is also capable of identifying a feature of a marker region in the scalogram, such as at least one characteristic feature positioned at one or more scales above or below the pulse band.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features of the present disclosure, its nature and various advantages will be more apparent upon consideration of the following detailed description, taken in conjunction with the accompanying drawings in which.

DETAILED DESCRIPTION

Figure 1:
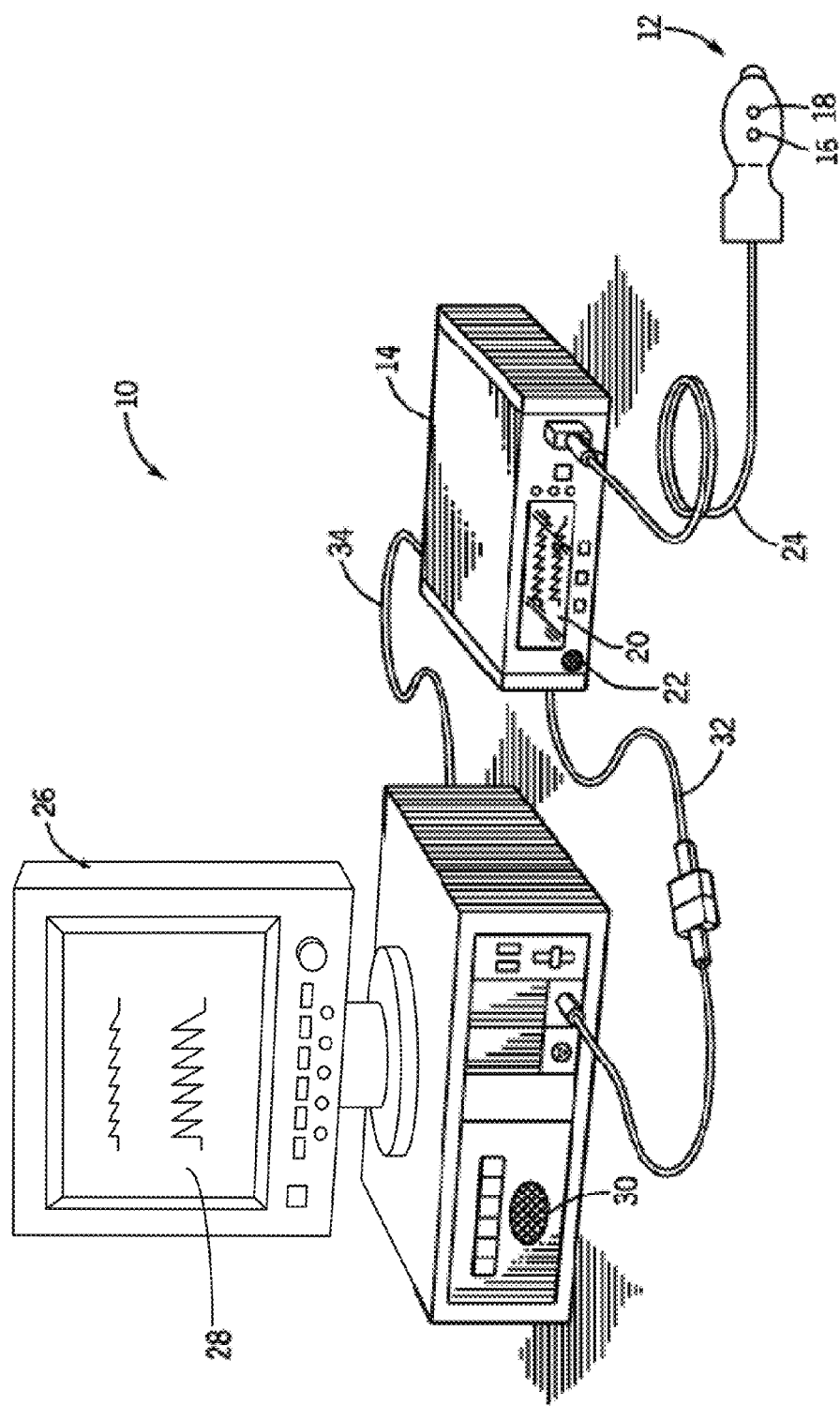
FIG. 1 is a perspective view of a pulse oximetry system.

In medicine, a plethysmograph is an instrument that measures physiological parameters, such as variations in the size of an organ or body part, through an analysis of the blood passing through or present in the targeted body part, or a depiction of these variations. An oximeter is an instrument that may determine the oxygen saturation of the blood. One common type of oximeter is a pulse oximeter, which determines oxygen saturation by analysis of an optically sensed plethysmograph.

A pulse oximeter is a medical device that may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A graph of light intensity versus time may be referred to as the photoplethysmogram. The light intensity or the amount of light absorbed may then used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda, t) = I_o(\lambda)\exp(-(s\beta_o(\lambda)+(1-s)\beta_r(\lambda))l(t)) \tag{1}$$

where:
$\lambda$=wavelength
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

$$\log I = \log I_o - (s\beta_o + (1-s)\beta_r)l \tag{2}$$

2. (2) is then differentiated with respect to time $$\frac{d\log I}{dt} = -(s\beta_o + (1-s)\beta_r)\frac{dl}{dt} \tag{3}$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda,t)}{dt} \simeq \log I(\lambda, t_2) - \log I(\lambda, t_1)$$

Using log A−log B=log A/B, $$\frac{d\log I(\lambda,t)}{dt} \simeq \log\left(\frac{I(t_2,\lambda)}{I(t_1,\lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1,\lambda_R)}{I(t_2,\lambda_R)}\right)}{\log\left(\frac{I(t_1,\lambda_{IR})}{I(t_2,\lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2,\lambda_R) - I(t_1,\lambda_R)}{I(t_1,\lambda_R)}}{\frac{I(t_2,\lambda_{IR}) - I(t_1,\lambda_{IR})}{I(t_1,\lambda_{IR})}} \quad (7)$$

$$= \frac{[I(t_2,\lambda_R) - I(t_1,\lambda_R)]I(t_1,\lambda_{IR})}{[I(t_2,\lambda_{IR}) - I(t_1,\lambda_{IR})]I(t_1,\lambda_R)}$$

$$= R$$

which defines a cluster of points whose slope of y versus x will give R where $$x(t)=[I(t_2,\lambda_{IR})-I(t_1,\lambda_{IR})]I(t_1,\lambda_R)$$

$$y(t)=[I(t_2,\lambda_R)-I(t_1,\lambda_R)]I(t_1,\lambda_{IR})$$

$$y(t)=Rx(t) \quad (8)$$

The optical signal through the tissue can be degraded by noise and motion artifact, among other sources. One source of noise is ambient light which reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, since blood is a fluid, it responds differently than the surrounding tissue to inertial effects, thus resulting in momentary changes in volume at the point to which the oximeter probe is attached.

Motion artifact can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

FIG. 1 is a perspective view of an embodiment of a pulse oximetry system 10. The system 10 includes a sensor 12 and a pulse oximetry monitor 14. The sensor 12 includes an emitter 16 for emitting light at two or more wavelengths into a patient's tissue. A detector 18 is also provided in the sensor 12 for detecting the light originally from the emitter 16 that emanates from the patient's tissue after passing through the tissue.

According to another embodiment and as will be described, the system 10 may include a plurality of sensors forming a sensor array in lieu of the single sensor 12. Each of the sensors of the sensor array may be a complementary metal oxide semiconductor (CMOS) sensor. Alternatively, each sensor of the array may be charged coupled device (CCD) sensor. In yet another embodiment, the sensor array may be made up of a combination of CMOS and CCD sensors. The CCD sensor comprises a photoactive region and a transmission region for receiving and transmitting data while the CMOS sensor is made up of an integrated circuit having an array of pixel sensors. Each pixel has a photodetector and an active amplifier.

According to an embodiment, the emitter 16 and detector 18 may be on opposite sides of a digit such as a finger or toe, in which case the light that is emanating from the tissue has passed completely through the digit. In an embodiment, the emitter 16 and detector 18 may be arranged so that light from the emitter 16 penetrates the tissue and is reflected by the tissue into the detector 18, such as a sensor designed to obtain pulse oximetry data from a patient's forehead.

In an embodiment, the sensor or sensor array may be connected to and draw its power from the monitor 14 as shown. In another embodiment, the sensor may be wirelessly connected to the monitor 14 and include its own battery or similar power supply (not shown). The monitor 14 may be configured to calculate physiological parameters based on data received from the sensor 12 relating to light emission and detection. In an alternative embodiment, the calculations may be performed on the monitoring device itself and the result of the oximetry reading is simply passed to the monitor 14. Further, the monitor 14 includes a display 20 configured to display the physiological parameters or other information about the system. In the embodiment shown, the monitor 14 also includes a speaker 22 to provide an audible sound that may be used in various other embodiments, such as for example, sounding an alarm in the event that a patient's physiological parameters are not within a predefined normal range.

In an embodiment, the sensor 12, or the sensor array, is communicatively coupled to the monitor 14 via a cable 24. However, in other embodiments a wireless transmission device (not shown) or the like may be utilized instead of or in addition to the cable 24.

In the illustrated embodiment, the pulse oximetry system 10 also includes a multi-parameter patient monitor 26. The monitor may be cathode ray tube type, a flat panel display (as shown) such as a liquid crystal display (LCD) or a plasma display, or any other type of monitor now known or later developed. The multi-parameter patient monitor 26 may be configured to calculate physiological parameters and to provide a central display 28 for information from the monitor 14 and from other medical monitoring devices or systems (not shown). For example, the multiparameter patient monitor 26 may be configured to display an estimate of a patient's blood oxygen saturation generated by the pulse oximetry monitor 14 (referred to as an "SpO$_2$" measurement), pulse rate information from the monitor 14 and blood pressure from a blood pressure monitor (not shown) on the display 28.

The monitor 14 may be communicatively coupled to the multi-parameter patient monitor 26 via a cable 32 or 34 coupled to a sensor input port or a digital communications port, respectively and/or may communicate wirelessly (not shown). In addition, the monitor 14 and/or the multi-parameter patient monitor 26 may be connected to a network to enable the sharing of information with servers or other workstations (not shown). The monitor 14 may be powered by a battery (not shown) or by a conventional power source such as a wall outlet.

Figure 2:
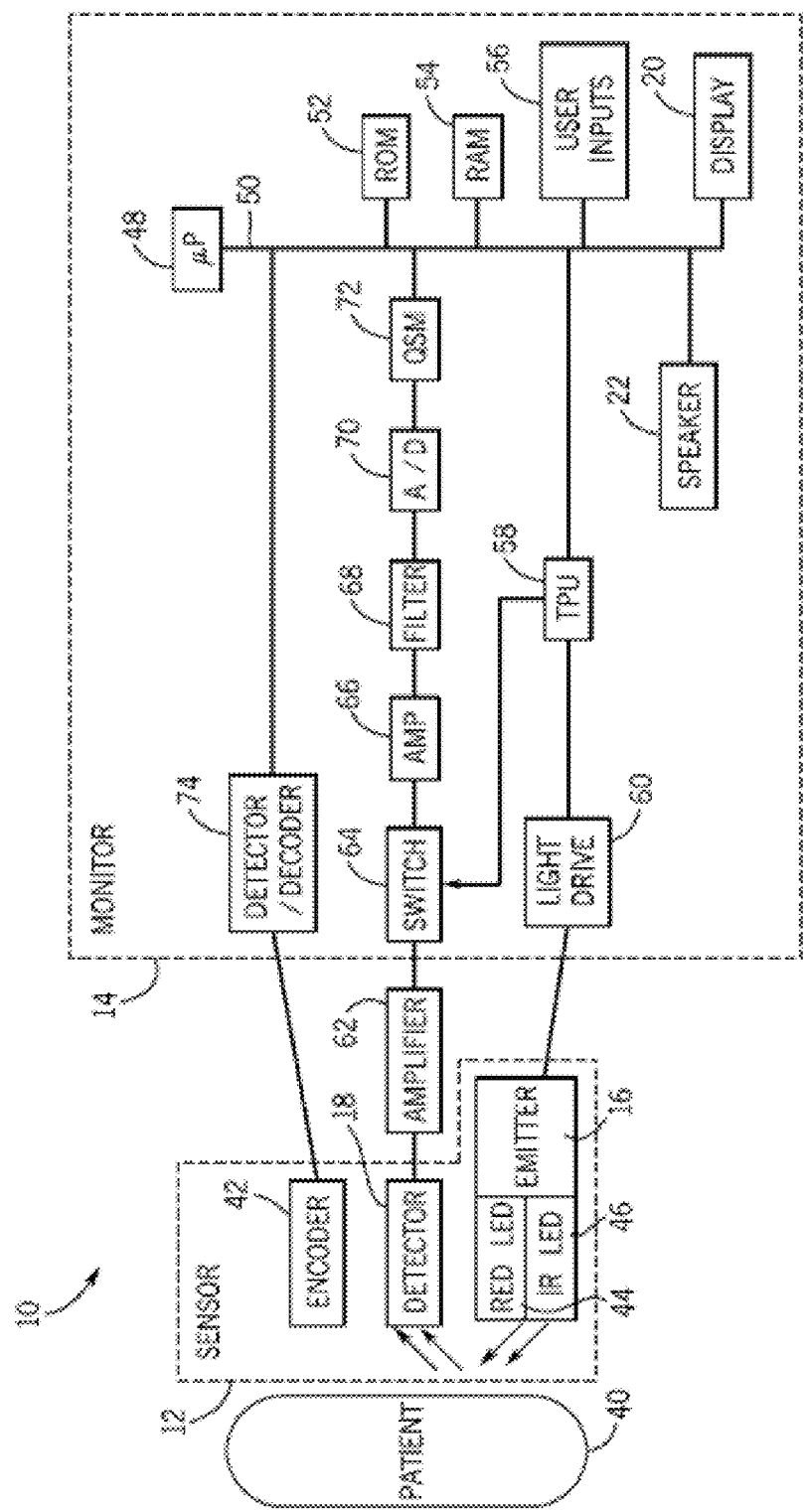
FIG. 2 is a block diagram of the exemplary pulse oximetry system of FIG. 1 coupled to a patient.

FIG. 2 is a block diagram of the embodiment of a pulse oximetry system 10 of FIG. 1 coupled to a patient 40 in accordance with present embodiments. Specifically, certain components of the sensor 12 and the monitor 14 are illustrated in FIG. 2. The sensor 12 includes the emitter 16, the detector 18, and an encoder 42. In the embodiment shown, the emitter 16 is configured to emit at least two wavelengths of light, e.g., RED and IR, into a patient's tissue 40. Hence, the emitter 16 may include a RED light emitting light source such as the RED light emitting diode (LED) 44 shown and an IR light emitting light source such as the IR LED 46 shown for emitting light into the patient's tissue 40 at the wavelengths used to calculate the patient's physiological parameters. In certain embodiments, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It should be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein light may also include any wavelength within the radio, microwave, infrared, visible, ultraviolet, or X-ray spectra, and that any suitable wavelength of electromagnetic radiation may be appropriate for use with the present techniques. Similarly, detector 18 may be chosen to be specifically sensitive to the chosen targeted energy spectrum of the emitter 16.

In an embodiment, the detector 18 may be configured to detect the intensity of light at the RED and IR wavelengths. Alternatively, each sensor in the array may be configured to detect an intensity of a single wavelength. In operation, light enters the detector 18 after passing through the patient's tissue 40. The detector 18 converts the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, the detector 18 sends the signal to the monitor 14, where physiological parameters may be calculated based on the absorption of the RED and IR wavelengths in the patient's tissue 40. An example of a device configured to perform such calculations is the Model N600x pulse oximeter available from Nellcor Puritan Bennett LLC.

In an embodiment, the encoder 42 may contain information about the sensor 12, such as what type of sensor it is (e.g., whether the sensor is intended for placement on a forehead or digit) and the wavelengths of light emitted by the emitter 16. This information may be used by the monitor 14 to select appropriate algorithms, lookup tables and/or calibration coefficients stored in the monitor 14 for calculating the patient's physiological parameters.

In addition, the encoder 42 may contain information specific to the patient 40, such as, for example, the patient's age, weight, and diagnosis. This information may allow the monitor 14 to determine patient-specific threshold ranges in which the patient's physiological parameter measurements should fall and to enable or disable additional physiological parameter algorithms. The encoder 42 may, for instance, be a coded resistor which stores values corresponding to the type of the sensor 12 or the type of each sensor in the sensor array, the wavelengths of light emitted by the emitter 16 on each sensor of the sensor array, and/or the patient's characteristics. In another embodiment, the encoder 42 may include a memory on which one or more of the following information may be stored for communication to the monitor 14: the type of the sensor 12; the wavelengths of light emitted by the emitter 16; the particular wavelength each sensor in the sensor array is monitoring; and a signal threshold for each sensor in the sensor array.

In an embodiment, signals from the detector 18 and the encoder 42 may be transmitted to the monitor 14. In the embodiment shown, the monitor 14 includes a general-purpose microprocessor 48 connected to an internal bus 50. The microprocessor 48 is adapted to execute software, which may include an operating system and one or more applications, as part of performing the functions described herein. Also connected to the bus 50 are a read-only memory (ROM) 52, a random access memory (RAM) 54, user inputs 56, the display 20, and the speaker 22.

The RAM 54 and ROM 52 are illustrated by way of example, and not limitation. Any computer-readable media may be used in the system for data storage. Computer-readable media are capable of storing information that can be interpreted by the microprocessor 48. This information may be data or may take the form of computer-executable instructions, such as software applications, that cause the microprocessor to perform certain functions and/or computer-implemented methods. Depending on the embodiment, such computer-readable media may comprise computer storage media and communication media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 provides timing control signals to a light drive circuitry 60 which controls when the emitter 16 is illuminated and multiplexed timing for the RED LED 44 and the IR LED 46. The TPU 58 also controls the gating-in of signals from detector 18 through an amplifier 62 and a switching circuit 64. These signals are sampled at the proper time, depending upon which light source is illuminated. The received signal from the detector 18 may be passed through an amplifier 66, a low pass filter 68, and an analog-to-digital converter 70. The digital data may then be stored in a queued serial module (QSM) 72 (or buffer) for later downloading to the RAM 54 as the QSM 72 fills up. In one embodiment, there may be multiple separate parallel paths having the amplifier 66, the filter 68, and the A/D converter 70 for multiple light wavelengths or spectra received.

In an embodiment, the microprocessor 48 may determine the patient's physiological parameters, such as $SpO_2$ and pulse rate, using various algorithms and/or look-up tables based on the value of the received signals and/or data corresponding to the light received by the detector 18. Signals corresponding to information about the patient 40, and particularly about the intensity of light emanating from a patient's tissue over time, may be transmitted from the encoder 42 to a decoder 74. These signals may include, for example, encoded information relating to patient characteristics. The decoder 74 may translate these signals to enable the microprocessor to determine the thresholds based on algorithms or look-up tables stored in the ROM 52. The user inputs 56 may be used to enter information about the patient, such as age, weight, height, diagnosis, medications, treatments, and so forth. In certain embodiments, the display 20 may exhibit a list of values which may generally apply to the patient, such as, for example, age ranges or medication families, which the user may select using the user inputs 56.

The embodiments described herein may relate to determining one or more statistical parameters of data from which an estimated physiological parameter value has been determined. Statistical parameters associated with the physiological parameter may include parameters related to the accuracy of the estimated value such as error estimates and probability distributions of the data.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \qquad (9)$$

where $\psi^*(t)$ is the complex conjugate of the wavelet function $\psi(t)$, a is the dilation parameter of the wavelet and b is the location parameter of the wavelet. The transform given by equation (9) can be used to construct a representation of a signal on a transform surface. The transform may be regarded as a time-scale representation. Wavelets are composed of a range of frequencies, one of which may be denoted the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found in the general literature.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of multiple (e.g., on the order of tens, hundreds, thousands, or any other number) wavelets that are each scaled in accordance with scales of interest of a signal such that smaller scale components of a signal are transformed using wavelets scaled more compactly than wavelets used to extract larger scale components of the signal and the window size of data each wavelet gets applied to varies according to scale as well. Thus, a higher resolution transform is possible using continuous wavelets relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain. As a further example, to reconstruct a temporal signal requires integrating twice, across time and scale, in the wavelet domain while, conversely, one integration across frequency is required to derive a temporal signal from a spectral domain). It is well known in the art that, as well as amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \qquad (10)$$

where '||' is the modulus operator. The scalogram may be rescaled for useful purposes. One common rescaling is defined as $$S_R(a,b) = \frac{|T(a,b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \qquad (12)$$

where $f_c$, the characteristic frequency of the mother wavelet (i.e., at a=1), becomes a scaling constant and f is the representative or characteristic frequency for the wavelet at arbitrary scale a.

$$\psi(t)=\pi^{-1/4}(e^{j2\pi f_0 t}-e^{-(2\pi f_0)^2/2})e^{-t^2/2} \qquad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0>>0$ and can be ignored, in which case, the Morlet wavelet can be written in a simpler form as $$\psi(t) = \frac{1}{\pi^{1/4}} e^{j2\pi f_0 t} e^{-t^2/2} \qquad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0>>0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
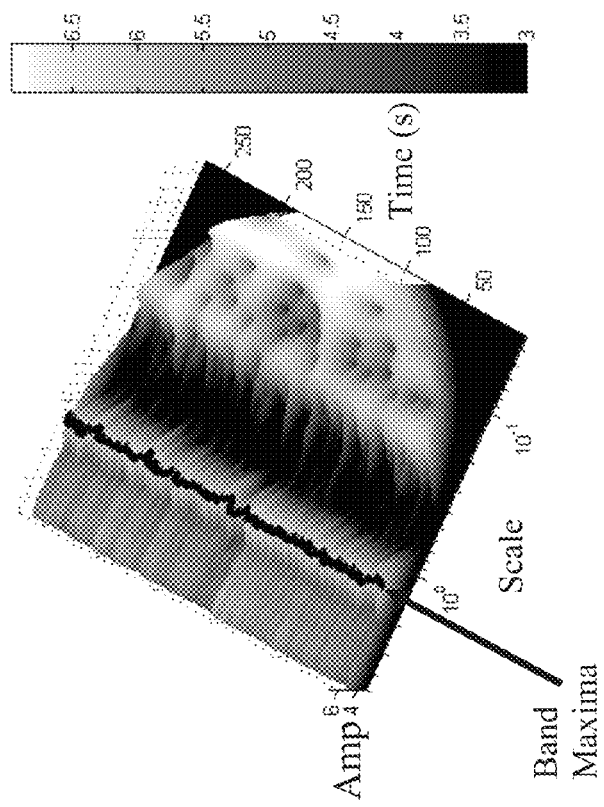
FIGS. 3(a) and 3(b) show illustrative views of a scalogram derived from a PPG signal in accordance with an embodiment.
Figure 3A:
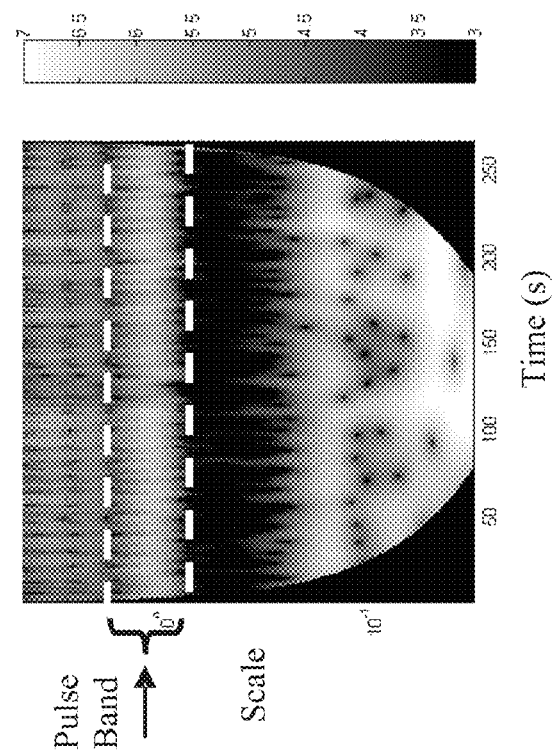

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) contain two views of a scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
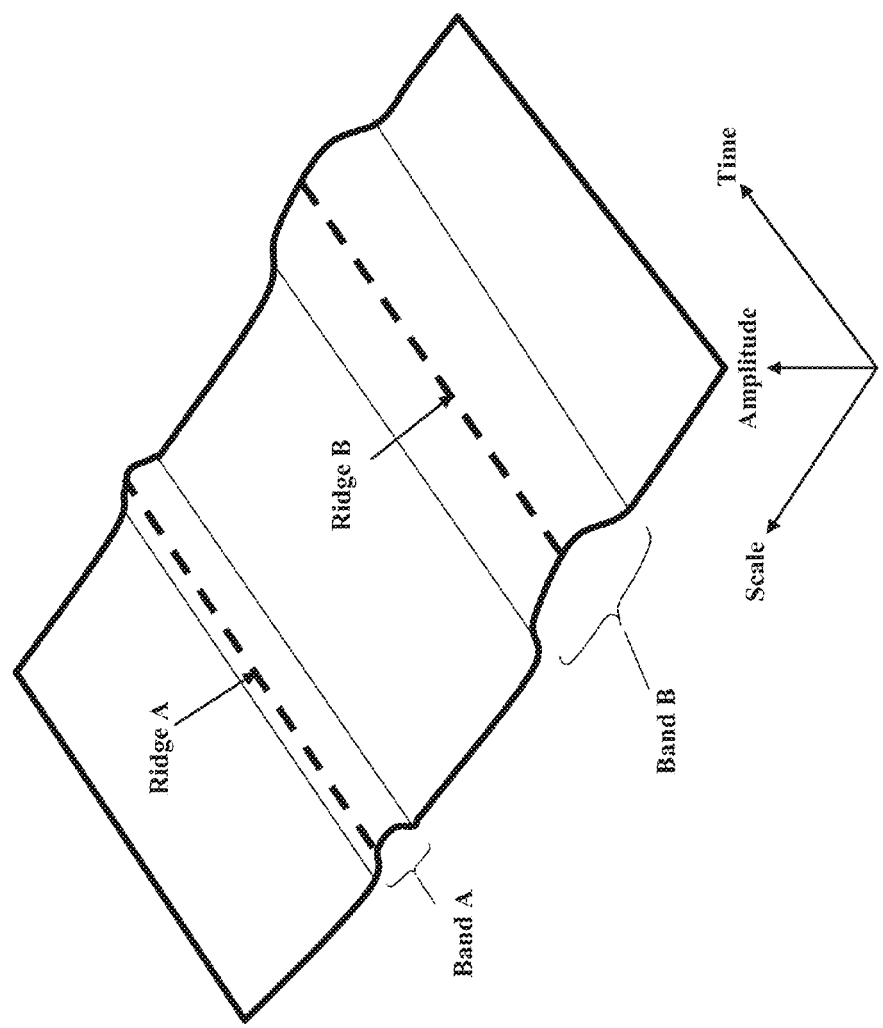
FIG. 3(c) shows an illustrative schematic of a wavelet transform of a signal containing two pertinent components in accordance with an embodiment.
Figure 3D:
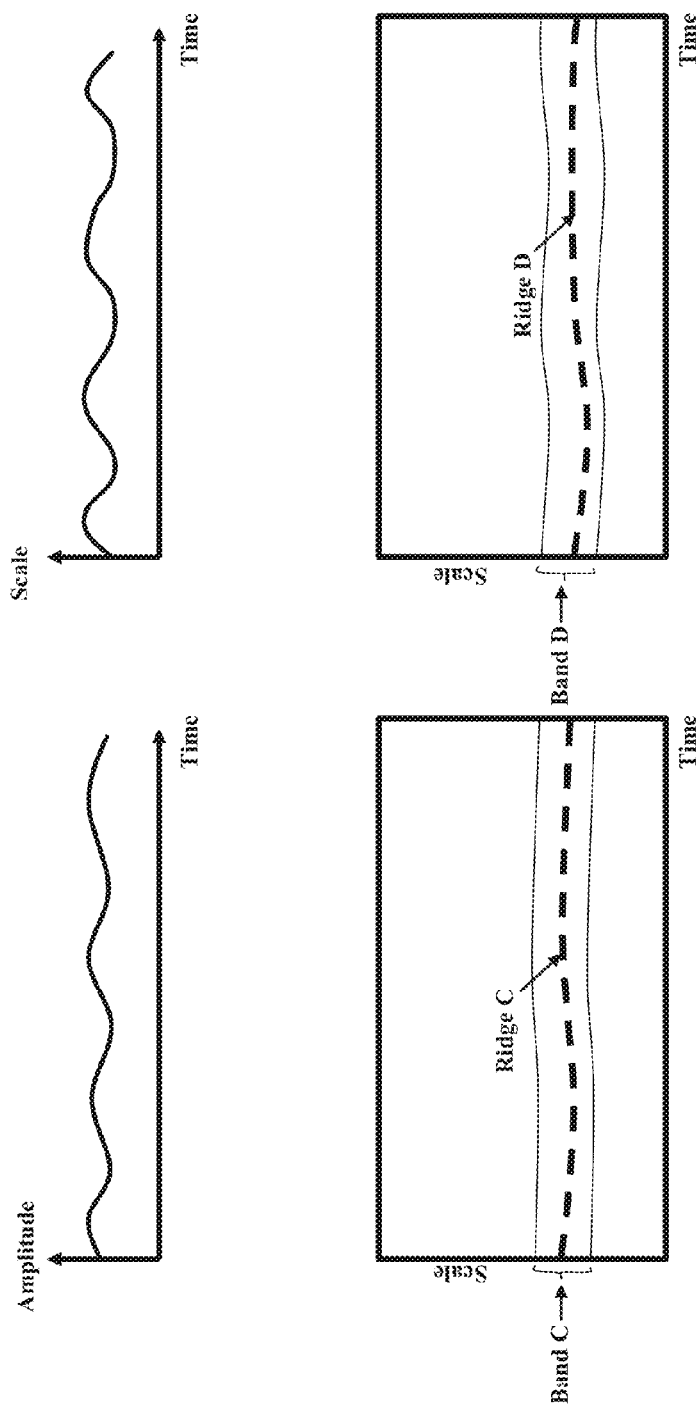
FIG. 3(d) shows an illustrative schematic of signals associated with a ridge in FIG. 3(c) and schematics of a further wavelet decomposition of these newly derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \quad \text{(a)}$$

which may also be written as:

$$x(t) = \frac{1}{C_g} \int_{-\infty}^{\infty} \int_0^{\infty} T(a,b) \psi_{a,b}(t) \frac{da\,db}{a^2} \quad \text{(b)}$$

where $C_g$ is a scalar value known as the admissibility constant. It is wavelet type dependent and may be calculated from:

$$C_g = \int_0^{\infty} \frac{|\hat{\psi}(f)|^2}{f} df \quad \text{(c)}$$

Figure 3E:
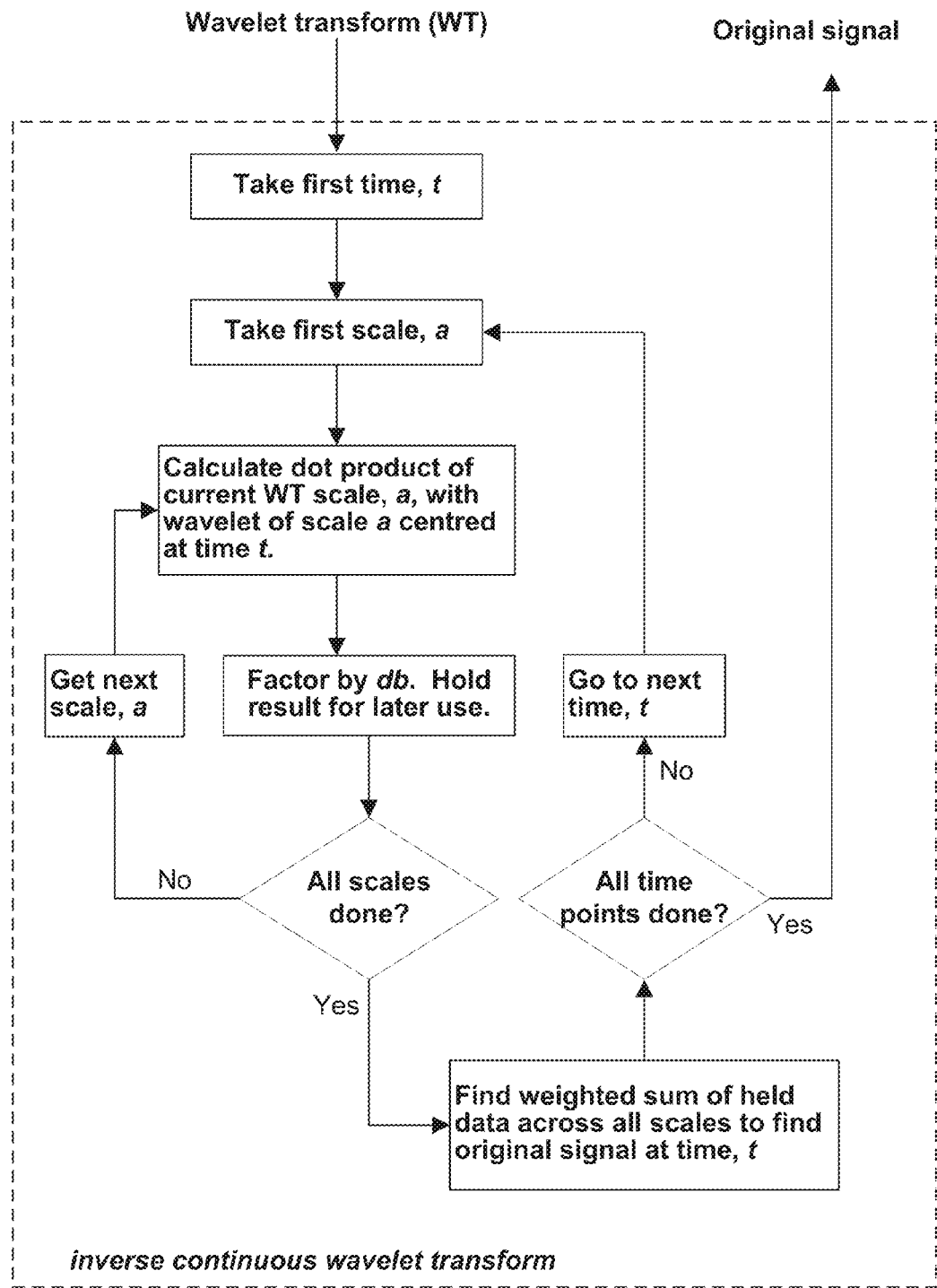
FIGS. 3(e) and 3(f) show flow charts of illustrative steps involved in performing an inverse continuous wavelet transform in accordance with embodiments.
Figure 3F:
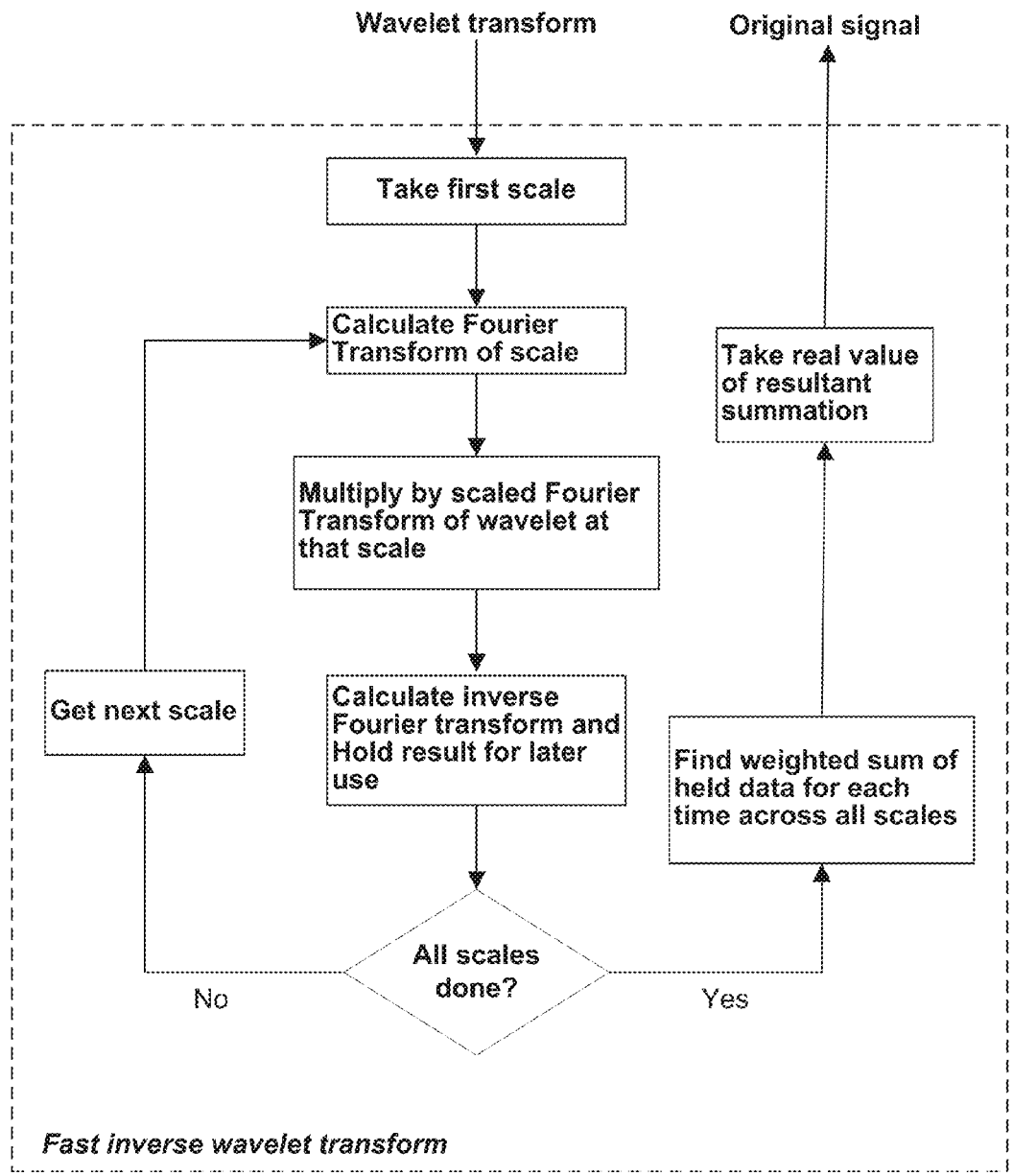

FIG. 3(e) is a flow chart of illustrative steps that may be taken to perform an inverse continuous wavelet transform in accordance with the above discussion. An approximation to the inverse transform may be made by considering equation (a) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform.

Figure 4:
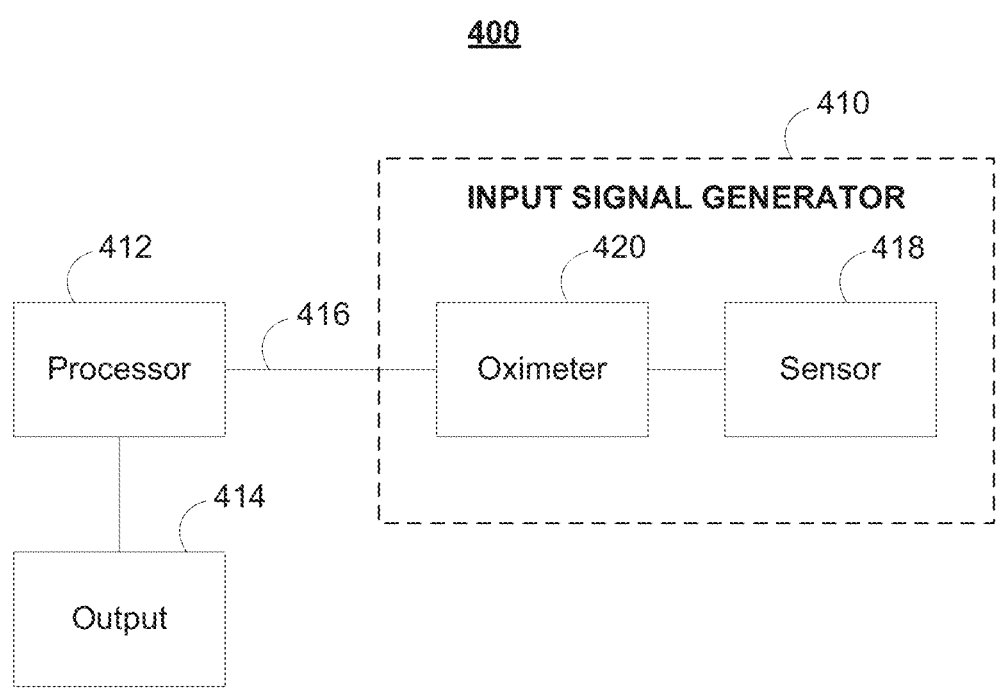
FIG. 4 shows an illustrative continuous wavelet processing system in accordance with some embodiments.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

One or more scalograms generated based on PPG signals using the methods described herein, such as by a wavelet transform, or other suitable method, may be used to evaluate signal quality (as well as, in the ordinary course, a physiological condition). In general, improved signal quality leads to more reliable information. Thus, when a patient is being monitored by monitor, an oximeter (such as oximeter 14 (FIG. 1), or other device, it is useful to evaluate the monitored data to ensure that the PPG signal is sensed optimally.

A scalogram derived from a person who is experiencing a medical condition or monitoring problem, may have different characteristics than a scalogram derived from a person who is not experiencing such a condition or problem. In addition, if the PPG signal is not sensed optimally because of problems with the monitoring system (e.g., a sensor location problem or inadequate light intensity), the scalogram will have characteristics that differ from those of a scalogram derived from a person that is being monitored optimally.

A scalogram derived from a healthy individual in a steady state condition may have a dominant pulse band with low amplitudes adjacent to the pulse band. FIG. 3(*c*), which is discussed above, shows an illustrative scalogram of a signal. If a PPG signal were used to generate the scalogram in FIG. 3(*c*), band A may be the pulse band and band B may be the respiration band. Pulse band A in FIG. 3(*c*) is an example of a dominant band with low amplitudes adjacent to the pulse band.

As mentioned previously, a monitor such as an oximeter 18 (FIG. 1) may be used to measure blood constituents, such as blood oxygen saturation levels. For some measurements, one or more sensors 12 (FIG. 1) of the oximeter may be optimally placed on a patient in a location that is near a site of highly perfused tissue away from large pulsating absorbers, such as an artery. One example of such a position is the forehead or above the eyebrows. The oximeter may pass light from an emitter, such as emitter 16 (FIG. 1), using a light source through blood perfused tissue and photoelectrically sense, for example using detector 18 (FIG. 1), the absorption of light in the tissue. For example, the oximeter 18 (FIG. 1) may measure the intensity of light that is received at the light sensor 12 (FIG. 1) as a function of time. A graph of light intensity versus time may be referred to as the photoplethysmogram. The light intensity or the amount of light absorbed may then used to calculate the amount of the blood constituent (e.g., oxyhemoglobin) being measured as well as the pulse rate and when each individual pulse occurs. For other types of measurements, such as a continuous non-invasive blood pressure measurement (CNIBP), a sensor (such as sensor 12 (FIG. 1) may be optimally placed near an artery. For some CNIBP measurements, two sensors may be used in two locations to measure a pulse transit time.

Figure 5:
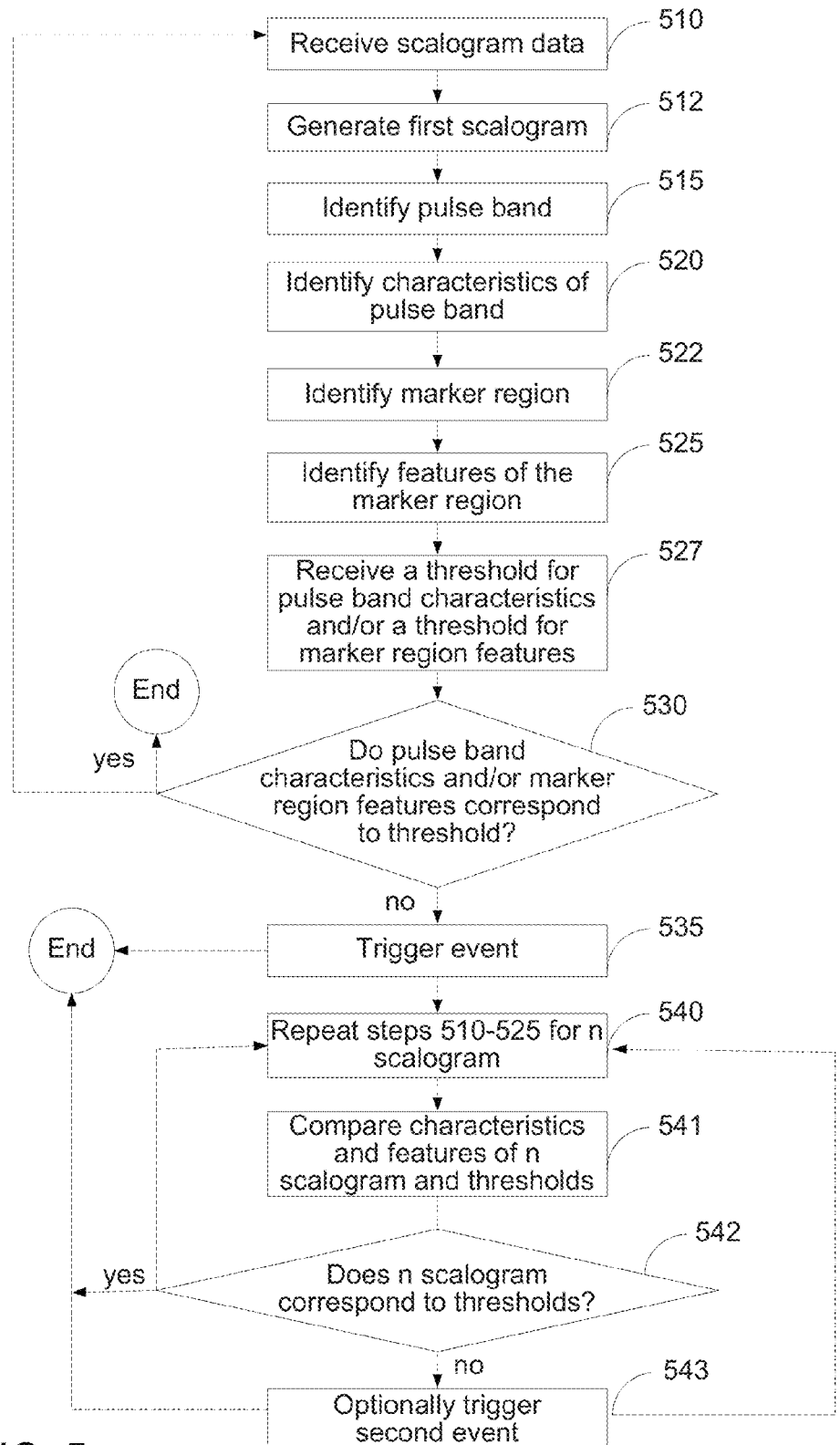
FIG. 5 shows an illustrative method of using a scalogram to determine a physiological condition in accordance with some embodiments.

FIG. 5 depicts an illustrative method according to an embodiment. A signal, such as a PPG signal (e.g., a red and/or infrared signal) is received at step 510. The signal may be any type of signal described herein, or as known to one of skill in the art, which may be transmitted by an oximeter (such as oximeter (14 of FIG. 1 or 420 of FIG. 4), a sensor (such as sensor 418 of FIG. 4 or sensor 12 of FIG. 1), or other device to a processor (such as processor 412 of FIG. 4). Transmission may be direct via cables 24 (FIG. 1), an intermediary component may be used, or other appropriate transmission means may also be used. The examples herein generally relate to an oximeter or blood pressure signals, but other signals may also be used. A scalogram of the received signal is generated at step 512, using a wavelet transform (e.g., a continuous wavelet transform), or other techniques described herein or known to one of skill in the art. The generated scalogram is typically one similar to those described herein, such as the scalogram depicted in FIGS. 3(*a*) & 3(*b*). The scalogram may be generated using one or more processors, such as oximeter microprocessor 48 (FIG. 2), processor 412 (FIG. 4), or other networked computers and processors. A pulse band of the scalogram may be identified at step 515 via the same or other processors used to generate the scalogram at step 512. The pulse band may be identified by the processor, based at least in part on an analysis of the scalogram data and/or the received signal from the sensor (such as sensor 12 (FIG. 1). For example, the pulse band may be identified using ridge following techniques on the scalogram.

Characteristics of the pulse band are determined at step 520, by a processor, such as the processor used to identify the pulse band at step 515, more specifically oximeter microprocessor 48 (FIG. 2), processor 412 (FIG. 4), or other networked computers and processors, or other component. Some of the determined characteristics of the pulse band may include, for example, strength of the pulse band, one or more shapes of the pulse band, characteristic features near the pulse band, or other features or characteristics. One way such pulse band characteristics may be determined is via incremental slices of the pulse band which may reveal the shape of the pulse band, amplitude and other features of the pulse band. The incremental slices and segments, and other calculations may be performed by analysis of the scalogram and pulse band data via the processor (such as oximeter microprocessor 48 (FIG. 2), processor 412 (FIG. 4), or other networked computers and processors) by taking one or more incremental samples of data received from the oximeter or sensor that indicates a pulse band in a scalogram.

Figure 5C:
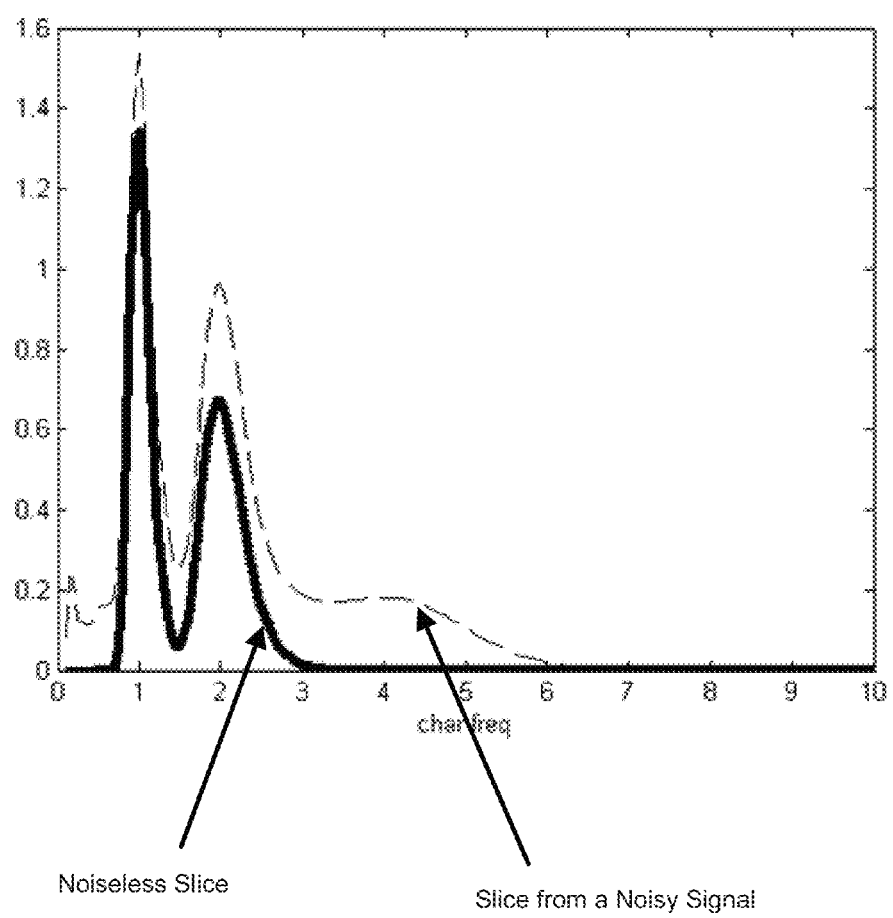
FIG. 5(c) shows an illustrative section of a pulse band of a scalogram in accordance with an embodiment.
Figure 5D:
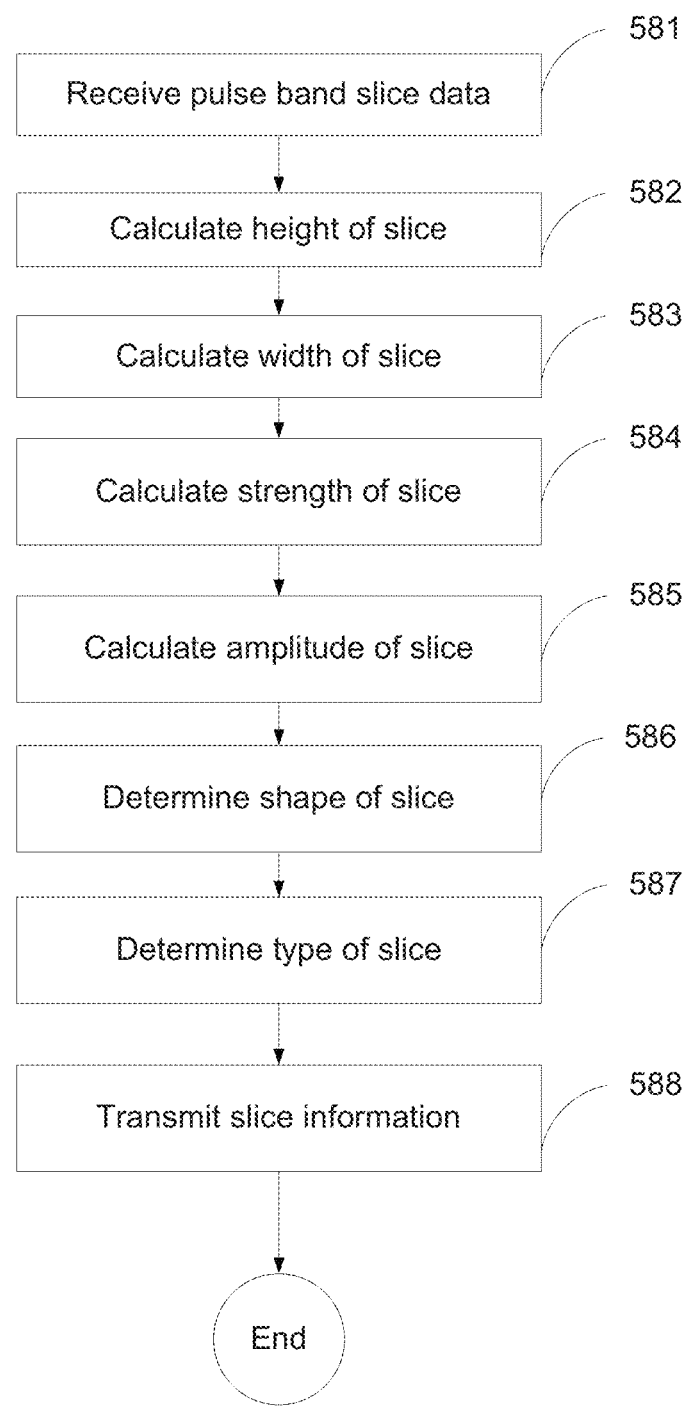
FIG. 5(d) shows an illustrative method for determining a characteristics of a pulse band in accordance with some embodiments.
Figure 6A:
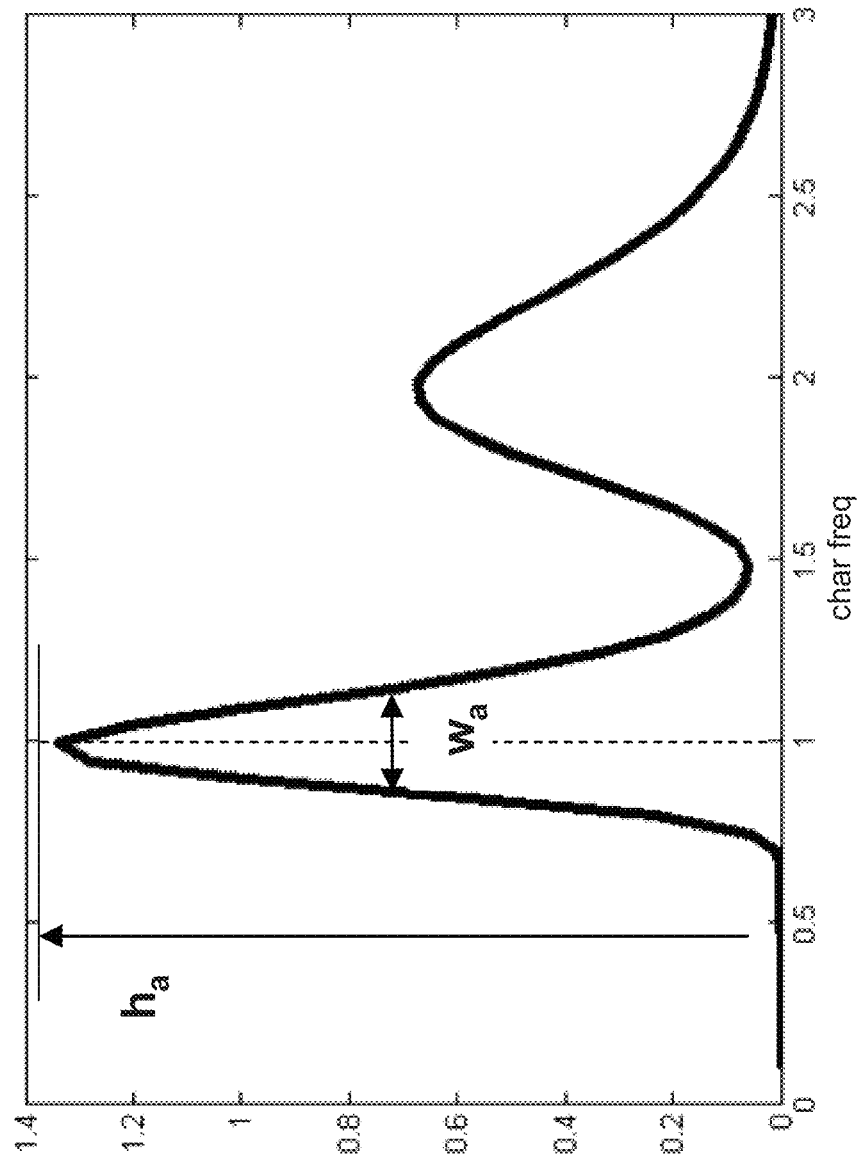
FIGS. 6(a) and 6(b) show illustrative sections of a pulse band of scalograms derived from a PPG signal in accordance with an embodiment.
Figure 6B:
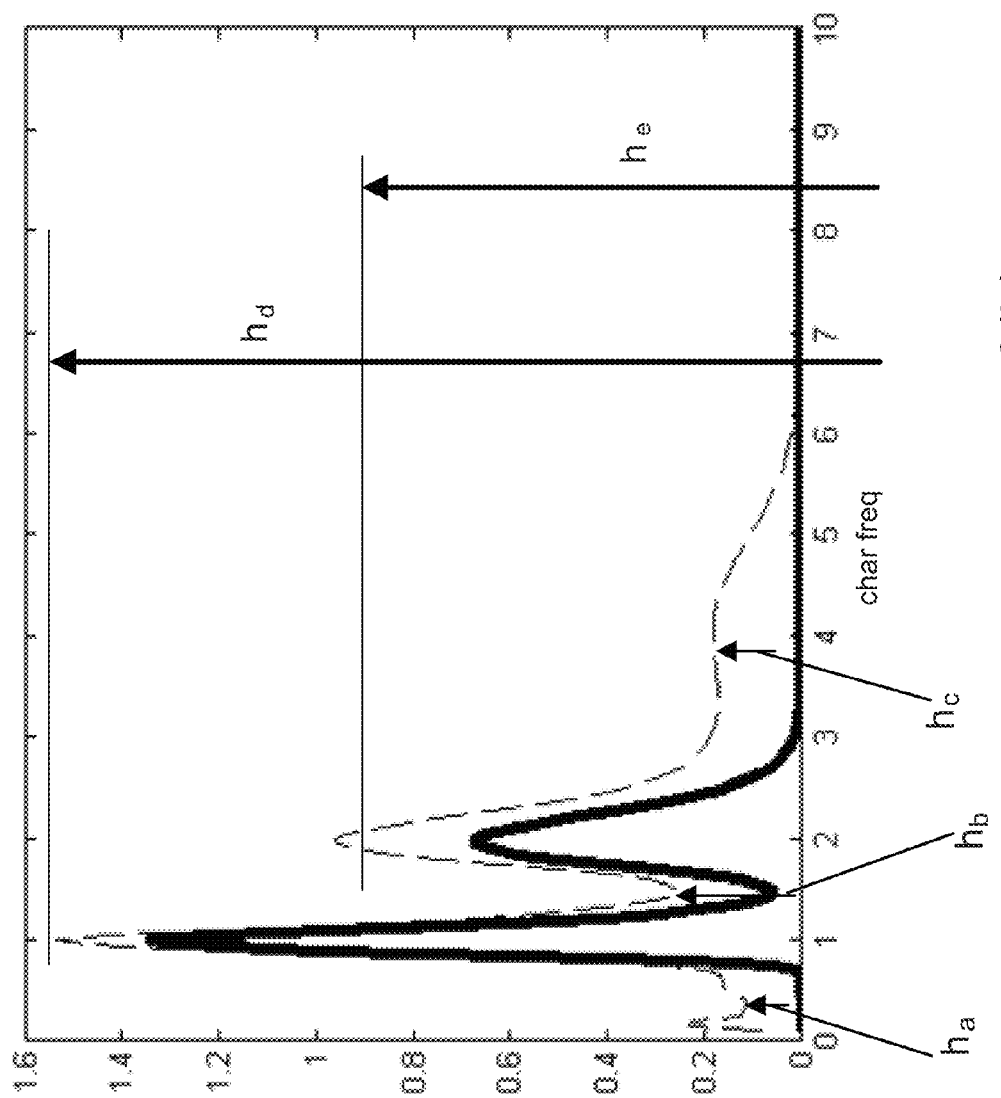

Examples of illustrative scalograms and a representative slice are depicted in FIGS. 5(*a*)-(*c*). FIG. 5(*d*) depicts a flow diagram for identifying characteristics of the pulse band, which may be used at step 520 (FIG. 5). As shown, pulse band slice data may be received at step 581. In general, the pulse band slice data may be received based on scalogram data provided by processor 412 (FIG. 4) based on a signal received from sensor 12 (FIG. 1), or oximeter 14 (FIG. 1) or 420 (FIG. 4) The pulse band slice data may be obtained using incremental segments of the pulse band data. One or more of steps 582-587 may be performed, in any combination, by a processor, such as processor 412 (FIG. 4) or microprocessor 48 (FIG. 2). At step 582 a height of the slice may be calculated by the processor by measuring a scale of the height of the slice. Representative slices of a pulse band which show an exemplary height and width are depicted in FIGS. 5(c), 6(a) & 6(b), which are discussed in detail below. At step 583 a width of a slice may be calculated by the processor by measuring a scale of the width of the slice. At step 584 a strength of the slice may be calculated by the processor by measuring an energy level of the slice. At step 585 amplitude of the slice may be calculated by the processor by measuring energy amplitude of the slice. At step 585 a shape of the slice may be determined by the processor by comparing the slice shape with one or more known slice shape types. At step 587 a type of slice may be determined by comparing type information measured by the processor with one or more known slice types. Other details relating to a pulse band may also be calculated or determined by the processor as would be understood by one of skill in the art. Other ways to determine features and characteristics of the pulse band include processing scalogram data using methods described herein and those known to one of skill in the art.

Figure 5A:
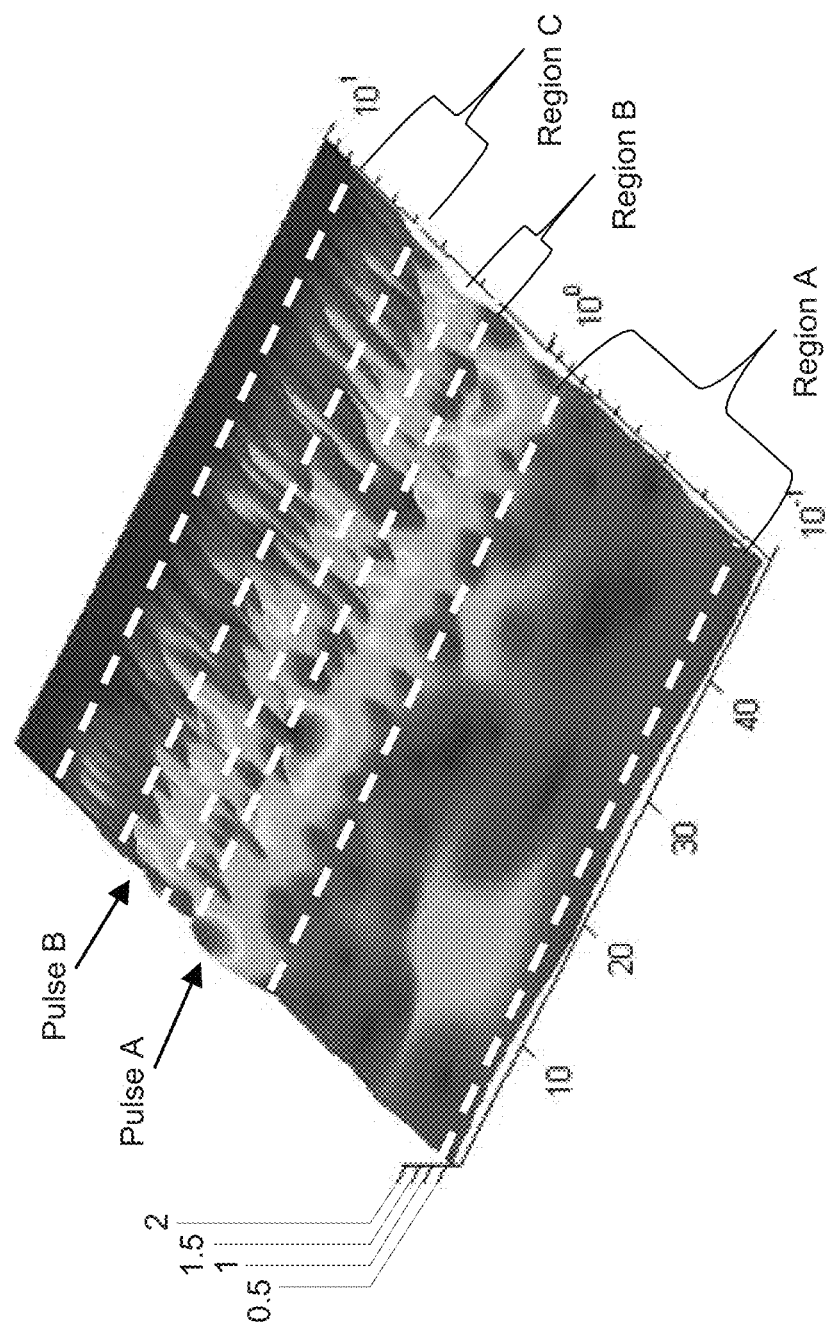
FIG. 5(a) shows an illustrative schematic of a wavelet transform of a signal in accordance with an embodiment.
Figure 5B:
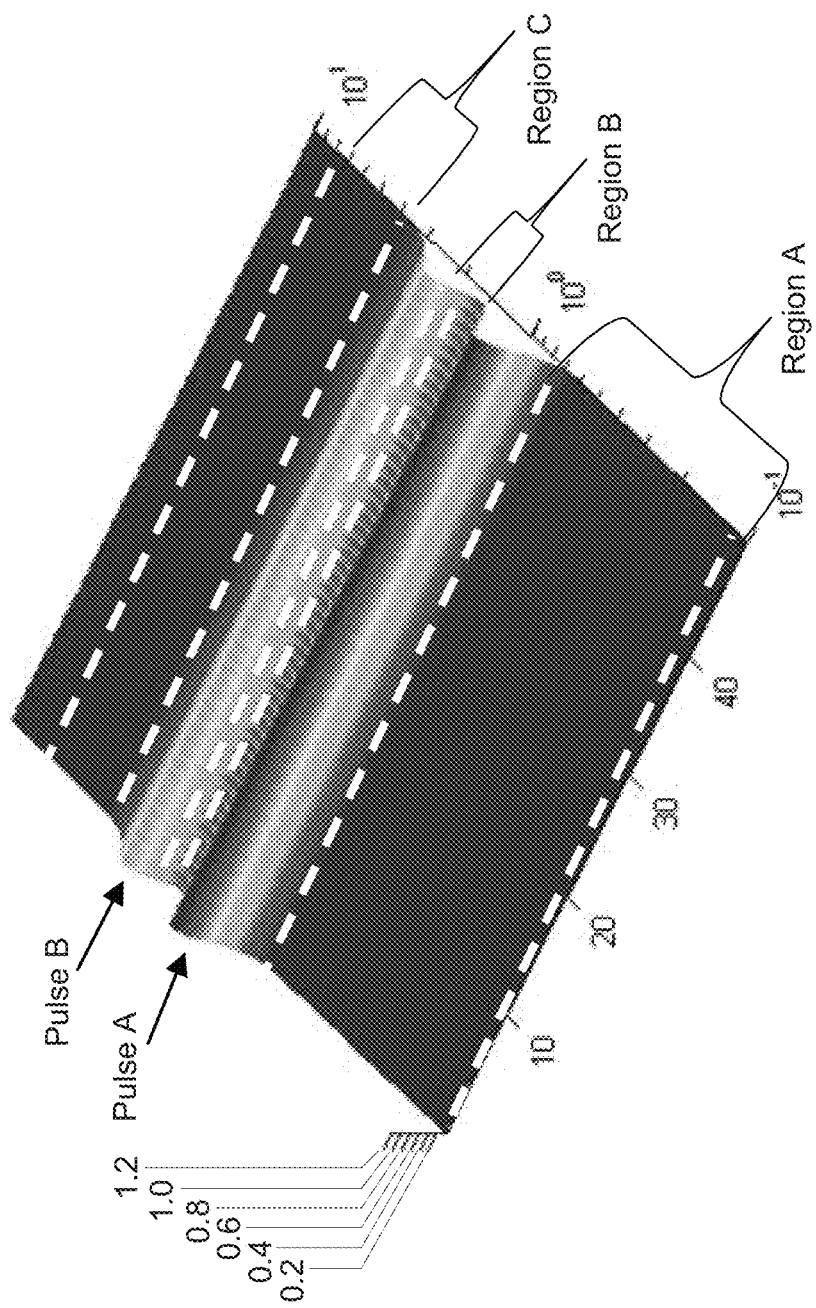
FIG. 5(b) shows an illustrative schematic of a wavelet transform of a signal in accordance with an embodiment.

In one illustrative example, FIG. 5(a) shows a scalogram of a synthetic signal pulse containing noise. In FIG. 5(a), bands associated with the pulse signal may be seen in the scalogram (FIG. 5(a) Pulse A and Pulse B). As shown, the bands associated with the pulse signal may be affected by noise and may be broken in form. In addition, regions of noise away from the pulse bands may be exhibited, e.g., as Regions A, B and C. FIG. 5(b) shows an illustrative equivalent scalogram from the same signal without noise present in the scalogram. The pulse bands (Pulse A and Pulse B FIG. 5(b)) in the noiseless scalogram may be smoothly connected.

A slice of a scalogram may be created by cutting through a band of the scalogram at a specific point in time. Alternatively, a slice may be created by summing over a region of the scalogram in time to obtain an average or weighted average of the slice. The slice may be generated or created using processor 412 (FIG. 4) or microprocessor 48 (FIG. 2).

FIG. 5(c) shows an illustrative weighted average slice taken from the synthetic signal scalograms in FIGS. 5(a) and 5(b). The dashed line in FIG. 5(c) corresponds to the noisy scalogram in FIG. 5(a) and the thick solid black line corresponds to the noiseless signal in FIG. 5(b). Decisions regarding the types of slices or segments may be performed by the processor (such as processor 412 (FIG. 4) or microprocessor 48 (FIG. 2), or other processor, or user selected. Each of the slices may be increments of a uniform time, or a combination of different time segments may also be used Each of the slices of the pulse band typically has a shape or other characteristic.

By building up a picture of the noiseless slice, a template of the noiseless signal may be obtained, (e.g., using processor 412 (FIG. 4) or microprocessor 48 (FIG. 2)), during periods when no noise is present. This can then be compared with the current slice information to see if there is a significant deviation indicative of the presence of noise. As shown in FIG. 5(c) the noisy slice profile deviates substantially from the noiseless slice profile over the whole region. The regions that are affected by the noise may depend on the noise characteristics. The noisy slice example in FIG. 5(c) may be from a Gaussian white noise with a energy distributed across all characteristic scales. Other types of noise may affect more localized regions. For example movement may affect only larger scales in the scalogram corresponding to lower characteristic frequencies (i.e., region A of FIG. 5(a)).

FIG. 6(a) depicts a simplified time slice of a pulseband of a scalogram showing a higher main band and secondary band both associated with the pulse. As shown, each time slice includes a pulse band height $h_a$ and width $w_a$. The size and shape of the pulse band or bands and other features adjacent to the pulse band or bands may provide an indication of signal quality. For example, a relatively higher height and/or wider width of a slice of the pulse band (e.g. as shown by the dashed line in FIG. 6(b)) may be an indication that the signal quality is low. The increase of the noise floor level between bands (e.g. $h_b$) and outside the band regions e.g. $h_a$ and $h_c$, or on the main pulse band (i.e. $h_d$) or a secondary band associated with the pulse morphology (e.g. $h_e$). This noise level may also affect the width of the main band and any secondary pulse bands as can be seen in the figures.

These and other calculations may be made by the processor (such as processor 412 (FIG. 4), or microprocessor 48 (FIG. 2)) using scalogram data as discussed herein. In some embodiments, a greater light intensity may be used to improve signal quality. In other embodiments, the size and shape of the pulse band may be used to assist an operator with sensor placement. For pulse oximetry, a desired location may produce a high and narrow pulse band. Alternatively for CNIBP applications, a desired location may produce an even taller and narrower pulse band, which may indicate that the sensor is located at or near an artery. (In this case a strong the arterial pulse may provide a poor ratio of ratios from the red and infrared signal and hence a poor SPO2 value, although provide a more dominant pulse for use in CNIBP.) This may be an optimal position for a CNIBP sensor. In other embodiments, a relative area underneath the pulse band slice, size, or amplitude of the pulse band may provide an indication of a physiological condition. Likewise the relative characteristics of bands within the time slice may provide clinically useful information. For example, for a finger PPG, a reduction in height of the secondary band with respect to the primary pulse band may indicate a reduction of peripheral resistance. Comparison and evaluation of the height and width of a slice of the pulse band may be performed by processor 412 (FIG. 4), or microprocessor 48 (FIG. 2)) and may be based on certain thresholds or standards, prior measurements and scalograms produced by the same or similar patient, or other technique. Such thresholds or standards may be device specific, user selected, or implemented via processor programming.

In some embodiments, analyzed aspects of the scalogram may include pulse band characteristics. In other embodiments, additional regions and features of the scalogram may also be analyzed, such as regions adjacent to the pulse band. In some embodiments, one or more marker regions may be identified at step 522 by a processor (processor 412 (FIG. 4), or microprocessor 48 (FIG. 2)) using scalogram data received from the oximeter 14 (FIG. 1), or other device. A processor may identify the marker regions based on scalogram data that, for example, indicates a characteristic feature having high amplitude regions adjacent to a pulse band. These regions may be referred to as marker regions. Features of the marker regions may be identified at step 525 using the processor. Some features of the marker regions include location, shape, spacing, type, and others and may be ascertained by the processor using algorithms and programming which may specify, for example, known features of marker regions. Marker regions may be spaced apart from the pulse band or may be an extension of the pulse band. Consecutive marker regions on the scalogram may be evenly spaced apart in time, randomly spaced apart in time, or the spacing may change over time. The marker regions may have any suitable shape such as, for example, rectangular, oval, square, circular, triangular, or a combination of shapes. In one example, the marker regions may be narrower in time, and longer in scale. The marker regions may also be identified using any other suitable technique.

In an embodiment, the marker regions and their sizes and shapes may be identified by using an amplitude threshold. The amplitude threshold may be predetermined or may dynamically change (e.g., as a function of the height and/or shape of the pulse band). The threshold may be selected by a user or programmed via the processor. In another embodiment, the marker regions may be identified by looking at changes in energy within one or more regions in the scalogram over time. In another embodiment, the processor may identify the marker regions using, for example, a rectangular region may be used and the energy within the region may be determined using any suitable methods such as by taking a median or average amplitude within the region or summing the amplitudes within the region. A marker region may also be identified by an increase and subsequent decrease in energy within the region over time. The marker regions may also be identified by using a combination of techniques. Regions A, B and C in FIG. 5(b) may be examples of marker regions. These may be set as the regions below the pulse band or secondary bands, above the pulse band or secondary bands, or between bands.

Figure 7A:
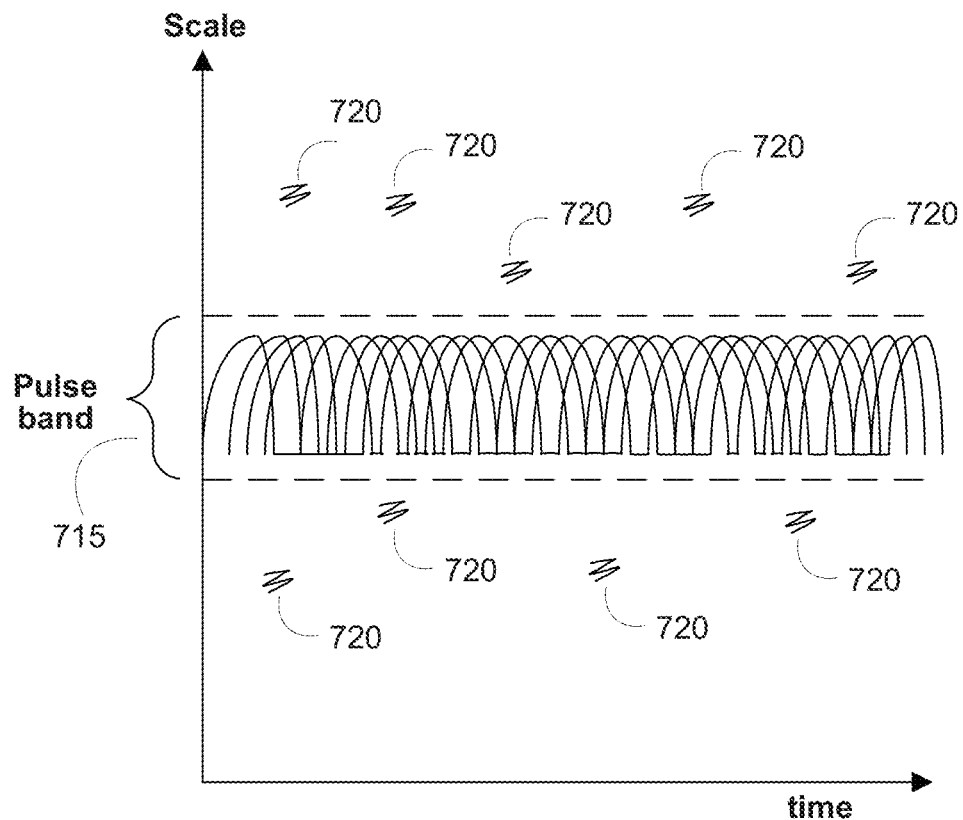
FIG. 7(a) shows an illustrative scalogram derived from a PPG signal in accordance with an embodiment.

As discussed herein, a patient's condition and/or monitoring signal quality may be evaluated by identifying and analyzing one or more characteristic features in a marker region in a scalogram. FIG. 7(a) shows a simplified scalogram 700 derived from a PPG signal. Scalogram 700 depicts pulse band 715 and characteristic features 720 on either side of pulse band 715. For clarity, scalogram 700 does not depict other features typically found in a scalogram of a PPG signal (e.g., the respiration band, noise, etc.). The characteristic features may be detected using one or more techniques, described above, typically via a processor 412 (FIG. 4) or microprocessor 48 (FIG. 2) using scalogram data. The characteristic features may be analyzed to determine their locations, sizes, shapes, amplitudes, and any other suitable characteristics. The presence or absence of characteristic features in a scalogram and their corresponding characteristics, alone or in combination with other scalogram and pulse band features discussed herein, may provide indications of a patient's condition and/or problems with the monitoring system. For example, the presence of characteristic features may be due to increased vascular peripheral resistance and their amplitudes relative to the pulse band amplitude may indicate a low perfusion while rapid and regular switching of precise scale regions may indicate cross-talk in the monitoring system.

Figure 7B:
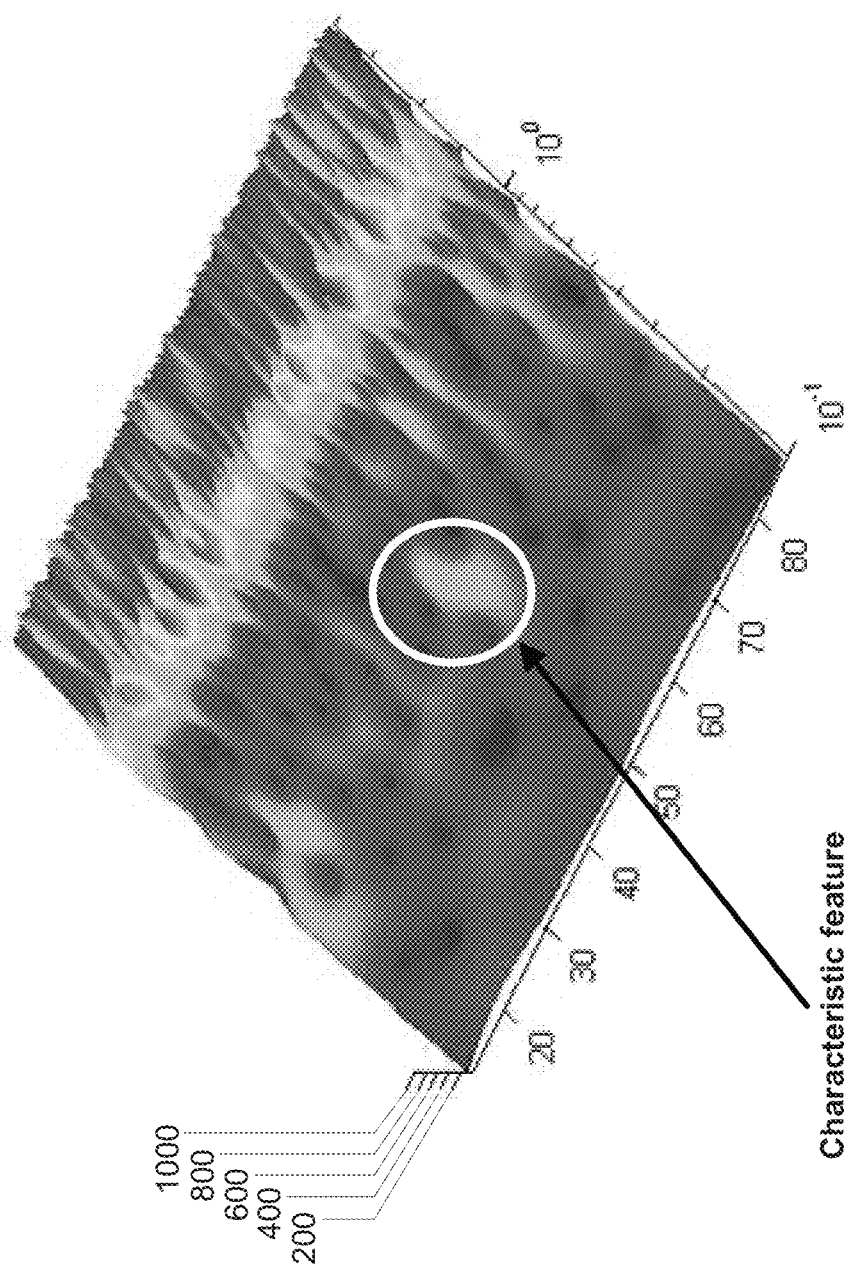
FIG. 7(b) shows an illustrative scalogram derived from a PPG signal in accordance with an embodiment.

FIG. 7(b) shows a characteristic feature circled in the plot. The characteristic feature may be a feature that occurs remote from the pulse band, which may be indicative of noise in the signal. Such characteristic features may be localized in time and scale as shown in FIG. 7(b) or may be stretched across scales if due to a sharp signal discontinuity, e.g. through rapid probe movement or replacement. The characteristic feature may also be stretched across times if due to longer term interference of the signal.

Turning again to FIG. 5, at step 527 one or more thresholds for pulse band characteristics and/or thresholds for marker region features may be received. The one or more thresholds are typically received by the processor 412 (FIG. 4), or microprocessor 48 (FIG. 2) via programming or user input. The threshold or base value can be related to a steady state scalogram value, and/or may be selected by a healthcare provider, or other user and entered via a user input (such as user input 56 (FIG. 2)). For example, a healthcare provider may select a base threshold, or such threshold may be included in programming for oximeter monitoring devices with one or more variations for patient condition, status, or other patient characteristic. Such threshold may be based on historical patient data, a scalogram derived from a patient having a good physiological condition and having optimal oximeter placement, or other threshold. Other types of thresholds can be based on an amplitude, location, type or shape of the characteristic feature or pulse band slice, a number of characteristic features, a height or width of the characteristic feature or pulse band slice, a combination of some or all of the aforementioned items, or other basis.

If one or more of the pulse band characteristics and/or marker region features are determined by the processor at step 530 to correspond to respective thresholds, the process flow can end, or optionally, steps 510-530 may be repeated to continue monitoring of signal quality. Correspondence to a threshold may mean, for example, that the characteristics are substantially similar to the threshold, or that the characteristics do not substantially exceed the threshold or do not substantially fail to reach the threshold.

If one or more of the pulse band characteristics and/or marker region features are determined by the processor at step 530 to not correspond to respective thresholds, an event may trigger at step 535. One type of event may be an alert, alarm or other indication that a light intensity of an optical signal may need change. More specific examples of an alert may include an indication of use of increased light intensity, an indication of use of decreased light intensity, an indication to move the sensor, an indication to move the sensor closer to an artery, an indication to move the sensor away from an artery, an indication that the sensor is not optimally located, an indication to examine a patient, and an indication of use of a second sensor. Other indications may also be provided. The indications and alerts may be generated as a control signal sent from the processor 412 (FIG. 4) to output 414 (FIG. 4) or to display 28 (FIG. 1), or other alarm. Alerts and indications may be provided as a user message, noise, light, or other alarm.

Another example of an event may be automatically changing a light intensity of the emitter 16 (FIG. 1) in a sensor 12 (FIG. 1) by, for example, sending a control signal from the processor 412 (FIG. 4) to the emitter 16 (FIG. 1) that is capable of changing light intensity or other light quality. Another event may be moving a sensor 12 (FIG. 1) or moving away from use of one sensor 12 (FIG. 1) to another sensor 12 (FIG. 1) if more than one sensor is used. The sensor may be moved to a point over a major artery or away from a major artery. Movement of the sensor may be performed by a user physically moving the sensor to another location. The sensor may also be moved automatically via any suitable means, such as a wheel or roller assembly that may be integrated in the sensor and controlled by the processor.

In some embodiments, after an event triggers, the process flow may end. In other embodiments, steps 510-525 may be repeated at step 540. In this scenario, additional scalogram data may be received following the event and characteristics of a second scalogram are obtained for comparison with the original scalogram at step 541. The components and methods for performing step 540 may be substantially similar to those described in connection with steps 510-525. Comparison of the characteristics and features of the original and second scalogram may be optionally performed to determine whether the second scalogram differs from the original. The second scalogram may also be compared to the thresholds (received at step 527) at step 541 using a processor (such as processor 412 (FIG. 4)). If the second scalogram is determined to correspond at step 542 to the thresholds received at step 527, the process flow may end. Alternatively, in some embodiments, the process flow may repeat at step 540 for continuous monitoring purposes. If the second scalogram is determined at step 542 not to correspond to thresholds, another event may trigger at step 543. For example, another alarm may be triggered at step 543, or a control signal for a different light intensity may be sent by the processor 412 (FIG. 4) to output 414 (FIG. 4), or other event. Other events may also be triggered. Following the second event, the process flow may end, or repeat at step 540 any number of n times for continuing monitoring. In some embodiments, following any event, a follow up routine may track changes in a subsequent scalogram, or portion of the scalogram, to confirm that, for example, there is a change between an original or base scalogram and a subsequent scalogram after the event. For example, when light intensity is changed in the optical signal (for example, by sending a control signal from the processor to the light), a scalogram or portions of a scalogram produced after the light intensity change may be evaluated by the processor, other component, or user, in comparison to the original scalogram or other standard or threshold to determine whether the light intensity change was appropriate or effective.

In another example, if a sensor (e.g., an oximeter sensor or a CNIBP sensor) is moved due to a shape (or other feature) of the pulse band, or because of the absence or presence of characteristic features, a following scalogram or portions of a scalogram may be evaluated by the processor (412 (FIG. 4) or microprocessor 48 (FIG. 2)) in comparison to the original scalogram or other standard or threshold to determine whether the move was effective. In a further example, following a triggering event, a scalogram or portions of a scalogram may be evaluated in comparison to the original scalogram or other standard or threshold to determine whether a subsequent event should be triggered. For example in a system that requires calibration under certain conditions, such as a CNIBP monitoring system, a comparison may be made to determine whether a recalibration is necessary.

In some embodiments, detection of one type of scalogram feature may be sufficient for triggering an event. In other embodiments, more than one type of scalogram feature may be necessary for triggering an event. Any combination of features, characteristics, and thresholds may be used as a basis for triggering an event. Such requirements may be programmed in the processor or user selected via user inputs 56 (FIG. 2).

The foregoing is merely illustrative of the principles of this disclosure and various modifications can be made by those skilled in the art without departing from the scope and spirit of the disclosure.

What is claimed is:

1. A method comprising:
using a processor for:
receiving a physiological signal;
transforming the physiological signal based at least in part on a wavelet transform;
generating scalogram data based at least in part on the transformed signal;
identifying a band in the scalogram data;
identifying a characteristic of the band;
identifying a noise floor of the scalogram data; and
determining signal quality of the physiological signal based at least in part on the characteristic of the band and the noise floor.

2. The method of claim 1 wherein the characteristic of the band comprises one or more of a height of the band, a width of the band, an amplitude of the band, a strength of the band, and a shape of the band.

3. The method of claim 1 wherein the characteristic of the band comprises a width of the band and wherein the signal quality of the physiological signal is inversely related to the width of the band.

4. The method of claim 1 wherein the characteristic of the band is identified by comparing a shape of the band with one or more shape types.

5. The method of claim 1 further comprising:
generating a template of a noiseless slice of the scalogram data based on the physiological signal during one or more periods when noise is not present; and
comparing current scalogram data with the template, wherein determining signal quality is further based at least in part on the comparison.

6. The method of claim 1 further comprising identifying a marker region corresponding to a high amplitude region adjacent to the band, wherein determining signal quality is further based at least in part on the marker region.

7. The method of claim 1 wherein the noise floor is identified outside of the band.

8. The method of claim 1 wherein identifying the noise floor comprises determining a minimum value between two bands in the scalogram data.

9. The method of claim 1 wherein the physiological signal comprises a photoplethysmograph signal.

10. The method of claim 9 wherein the band comprises a pulse band.

11. A system comprising:
a processor capable of:
receiving a physiological signal;
transforming the physiological signal based at least in part on a wavelet transform;
generating scalogram data based at least in part on the transformed signal;
identifying a band in the scalogram data;
identifying a characteristic of the band;
identifying a noise floor of the scalogram data; and
determining signal quality of the physiological signal based at least in part on the characteristic of the band and the noise floor; and
a display for displaying information based at least in part on the physiological signal.

12. The system of claim 11 wherein the characteristic of the band comprises one or more of a height of the band, a width of the band, an amplitude of the band, a strength of the band, and a shape of the band.

13. The system of claim 11 wherein the characteristic of the band comprises a width of the band and wherein the signal quality of the physiological signal is inversely related to the width of the band.

14. The system of claim 11 wherein the characteristic of the band is identified by comparing a shape of the band with one or more shape types.

15. The system of claim 11 wherein the processor is further capable of:
generating a template of a noiseless slice of the scalogram data based on the physiological signal during one or more periods when noise is not present; and
comparing current scalogram data with the template, wherein determining signal quality is further based at least in part on the comparison.

16. The system of claim 11 wherein the processor is further capable of identifying a marker region corresponding to a high amplitude region adjacent to the band, wherein determining signal quality is further based at least in part on the marker region.

17. The system of claim 11 wherein the noise floor is identified outside of the band.

18. The system of claim 11 wherein identifying the noise floor comprises determining a minimum value between two bands in the scalogram data.

19. The system of claim 11 wherein the physiological signal comprises a photoplethysmograph signal detected by a sensor.

20. The system of claim 19 wherein the band comprises a pulse band.

* * * * *